(12) United States Patent
Neumann

(10) Patent No.: US 11,581,084 B2
(45) Date of Patent: Feb. 14, 2023

(54) SYSTEMS AND METHODS FOR GENERATING AN ALIMENTARY PLAN FOR MANAGING SKIN DISORDERS

(71) Applicant: KPN INNOVATIONS, LLC., Lakewood, CO (US)

(72) Inventor: Kenneth Neumann, Lakewood, CO (US)

(73) Assignee: KPN INNOVATIONS, LLC., Lakewood, CO (US)

( * ) Notice: Subject to any disclaimer, the term of this patent is extended or adjusted under 35 U.S.C. 154(b) by 0 days.

(21) Appl. No.: 17/136,272

(22) Filed: Dec. 29, 2020

(65) Prior Publication Data

US 2022/0208344 A1    Jun. 30, 2022

(51) Int. Cl.
*G16H 20/60* (2018.01)
*G16H 50/30* (2018.01)
(Continued)

(52) U.S. Cl.
CPC ............ *G16H 20/60* (2018.01); *A61B 5/441* (2013.01); *A61B 5/7264* (2013.01); *G06N 3/08* (2013.01);
(Continued)

(58) Field of Classification Search
CPC ........ G16H 20/60; G16H 70/60; G16H 10/40; G16H 10/60; G16H 50/30; G16H 50/70;
(Continued)

(56) References Cited

U.S. PATENT DOCUMENTS 8,388,532 B2 * 3/2013 Morgan ............... A61B 5/7275
600/300
10,835,126 B1 * 11/2020 Cong .................. A61B 5/0075
(Continued)

FOREIGN PATENT DOCUMENTS

WO    2011087523 A1    7/2011

OTHER PUBLICATIONS

Pérez-Sánchez A, Barrajón-Catalán E, Herranz-López M, Micol V. Nutraceuticals for Skin Care: A Comprehensive Review of Human Clinical Studies. Nutrients. Mar. 24, 2018;10(4):403. doi: 10.3390/nu10040403. PMID: 29587342; PMCID: PMC5946188. (Year: 2018).*

(Continued)

*Primary Examiner* — Jay M. Patel
(74) *Attorney, Agent, or Firm* — Caldwell Intellectual Property Law

(57) ABSTRACT

A system for generating an alimentary plan is disclosed. The system comprises a computing device which is configured to receive an input that includes physiological data related to a skin sample. Computing device is configured to extract a plurality of biological indicators related to disease state from the physiological data. Computing device is configured to determine a biological indicator score for each biological score for each biological indicator of the plurality of biological indicators. Computing device is configured to generate a skin disorder classifier by receiving skin disorder training data. The computing device is configured to classify, using the skin disorder classifier, the at least one biological indicator and the biological indicator score to a positive result for a skin disorder. Computing device is configured to generate an alimentary plan as a function of the positive result. A method for generating an alimentary plan is also disclosed.

20 Claims, 7 Drawing Sheets

(51) Int. Cl.
*G16H 70/60* (2018.01)
*G16H 50/20* (2018.01)
*G16H 10/60* (2018.01)
*G16H 50/70* (2018.01)
*G06N 3/08* (2006.01)
*G16B 50/00* (2019.01)
*G16B 40/00* (2019.01)
*G16H 10/40* (2018.01)
*A61B 5/00* (2006.01)
*A61B 10/02* (2006.01)
*G06N 3/04* (2006.01)

(52) U.S. Cl.
CPC ............ *G16B 40/00* (2019.02); *G16B 50/00* (2019.02); *G16H 10/40* (2018.01); *G16H 10/60* (2018.01); *G16H 50/20* (2018.01); *G16H 50/30* (2018.01); *G16H 50/70* (2018.01); *G16H 70/60* (2018.01); *A61B 5/0077* (2013.01); *A61B 10/02* (2013.01); *G06N 3/04* (2013.01)

(58) Field of Classification Search
CPC ........ G16H 50/20; G16H 50/00; G16B 40/00; A61B 5/441; A61B 5/7264; G06N 3/08
See application file for complete search history.

(56) References Cited

U.S. PATENT DOCUMENTS

| | | | |
|---|---|---|---|
| 2002/0038310 A1* | 3/2002 | Reitberg | G16H 20/10 |
| 2007/0112585 A1* | 5/2007 | Breiter | G16B 40/20 |
| | | | 705/2 |
| 2010/0015110 A1* | 1/2010 | Kano | A61K 31/164 |
| | | | 424/93.44 |
| 2014/0072583 A1* | 3/2014 | Ardeleanu | A61K 31/58 |
| | | | 424/172.1 |
| 2016/0199427 A1* | 7/2016 | Yang | A23L 33/105 |
| | | | 424/767 |
| 2017/0228514 A1* | 8/2017 | Apte | G16B 50/30 |
| 2017/0262614 A1* | 9/2017 | Vishnubhatla | G16H 50/20 |
| 2018/0014777 A1* | 1/2018 | Amir | A61B 5/4839 |
| 2018/0122511 A1* | 5/2018 | Apte | G16H 50/20 |
| 2019/0012433 A1* | 1/2019 | Conway | G06T 20/00 |
| 2019/0021649 A1* | 1/2019 | Van Snellenberg | G06T 7/0012 |
| 2019/0065970 A1* | 2/2019 | Bonutti | G06N 5/045 |
| 2019/0381005 A1* | 12/2019 | Prybolsky | G16H 20/10 |
| 2019/0388016 A1* | 12/2019 | Lewis | A61B 5/441 |
| 2021/0027897 A1* | 1/2021 | Rasochova | A61B 5/0013 |

OTHER PUBLICATIONS

Title: Biomarkers: Potential Uses and Limitations Date: Apr. 2004 By: Dr. Richard Mayeux.

* cited by examiner

SYSTEMS AND METHODS FOR GENERATING AN ALIMENTARY PLAN FOR MANAGING SKIN DISORDERS

FIELD OF THE INVENTION

The present invention generally relates to the field of nutrition for disease management. In particular, the present invention is directed to a system and method for generating an alimentary plan.

BACKGROUND

Nutrition is an essential function of life as it provides the necessary nutrients the body needs to sustain all functions of life. The use of artificial intelligence in the field of nutrition may assist in the development and management of a healthy lifestyle for an individual.

SUMMARY OF THE DISCLOSURE

In an aspect of the disclosure, a system for generating an alimentary plan is disclosed. The system comprises a computing device which is configured to receive an input that includes physiological data related to a skin sample. Computing device is configured to extract a plurality of biological indicators from the physiological data. The plurality of biological indicators includes at least one biological indicator related to a disease state comprising at least one skin disorder. Computing device is configured to determine a biological indicator score for each biological score for each biological indicator of the plurality of biological indicators. Computing device is configured to generate a skin disorder classifier by receiving skin disorder training data correlating biological indicators of skin disorders and biological indicator scores to skin disorder labels. The skin disorder classifier is trained by using skin disorder training data. The computing device is configured to classify, using the skin disorder classifier, the at least one biological indicator and the biological indicator score to a positive result for a skin disorder. Computing device is configured to generate an alimentary plan as a function of the positive result.

In another aspect of the disclosure, a method for generating an alimentary plan is disclosed. The method comprises receiving, by a computing device, an input that includes physiological data related to a skin sample. The method extracts, by the computing device, a plurality of biological indicators from the physiological data. The plurality of biological indicators includes at least one biological indicator related to a disease state comprising at least one skin disorder. The method determines, by the computing device, a biological indicator score for each biological score for each biological indicator of the plurality of biological indicators. The method generates, by the computing device, a skin disorder classifier by receiving skin disorder training data correlating biological indicators of skin disorders and biological indicator scores to skin disorder labels. The skin disorder classifier is trained by using skin disorder training data. The method classifies, by the computing device and using the skin disorder classifier, the at least one biological indicator and the biological indicator score to a positive result for a skin disorder. The method generates, by the computing device, an alimentary plan as a function of the positive result.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for generating a meal plan to treat and prevent skin disorders. The system may include a computing device that may receive an input which may be in the form of a tissue, a slide, and the like. The tissue or slide may contain at least one biological indicator that may be indicative of a skin condition. Each biological indicator may come with a biological indicator score. The biological indicator score may be referenced from the literature or experimentally obtained. A classifier is trained and used to classify a biological indicator and a biological indicator score to a skin disorder. A positive result may generate an alimentary plan to treat and/or prevent the skin disorder.

A practical application of this technology includes the use of a machine-learning model to provide a user access to alimentary plans that may improve or prevent a skin disorder. The system and method allow for an update of the alimentary plan if the skin disorder does not improve.

Figure 1:
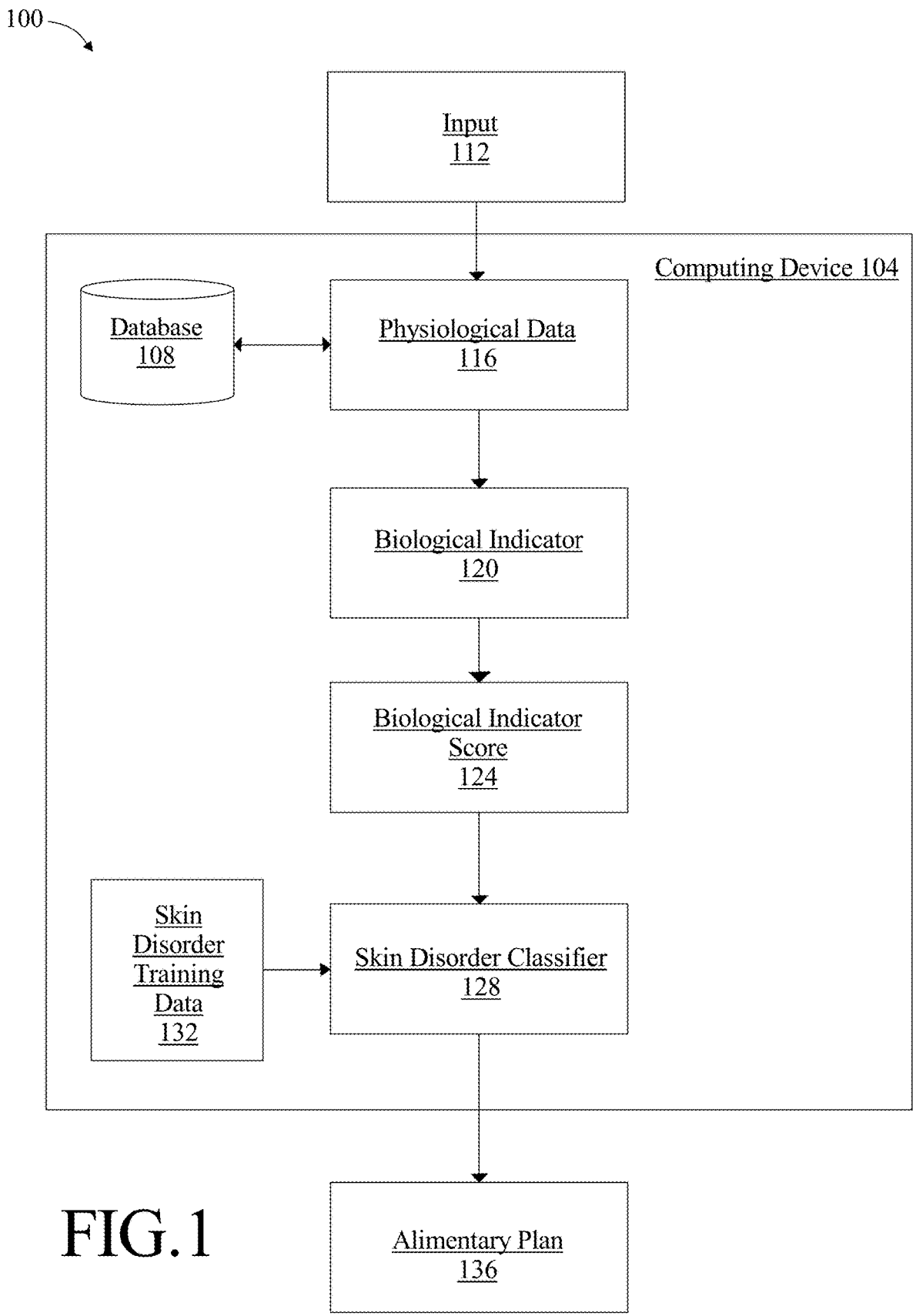
FIG. 1 is a block diagram of an exemplary embodiment of a system of determining an alimentary plan to manage a skin condition.

Referring now to FIG. 1, an exemplary embodiment of a system 100 for generating an alimentary plan for managing a skin disorder is illustrated. System includes a computing device 104. Computing device 104 may include any computing device as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting a computing device to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device.

With continued reference to FIG. 1, computing device 104 may be designed and/or configured to perform any method, method step, or sequence of method steps in any embodiment described in this disclosure, in any order and with any degree of repetition. For instance, Computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, computing device 104 may connect to and/or include a database 108. Database 108 may be implemented, without limitation, as a relational database 108, a key-value retrieval database 108 such as a NOSQL database 108, or any other format or structure for use as a database 108 that a person skilled in the art would recognize as suitable upon review of the entirety of this disclosure. Database 108 may alternatively or additionally be implemented using a distributed data storage protocol and/or data structure, such as a distributed hash table or the like. Database 108 may include a plurality of data entries and/or records as described above. Data entries in a database 108 may be flagged with or linked to one or more additional elements of information, which may be reflected in data entry cells and/or in linked tables such as tables related by one or more indices in a relational database 108. Persons skilled in the art, upon reviewing the entirety of this disclosure, will be aware of various ways in which data entries in a database 108 may store, retrieve, organize, and/or reflect data and/or records as used herein, as well as categories and/or populations of data consistently with this disclosure. In some embodiments, network data, or other information such as user information, transfer party information, and alimentary provider information, may be stored in and/or retrieved from database 108.

Figure 2:
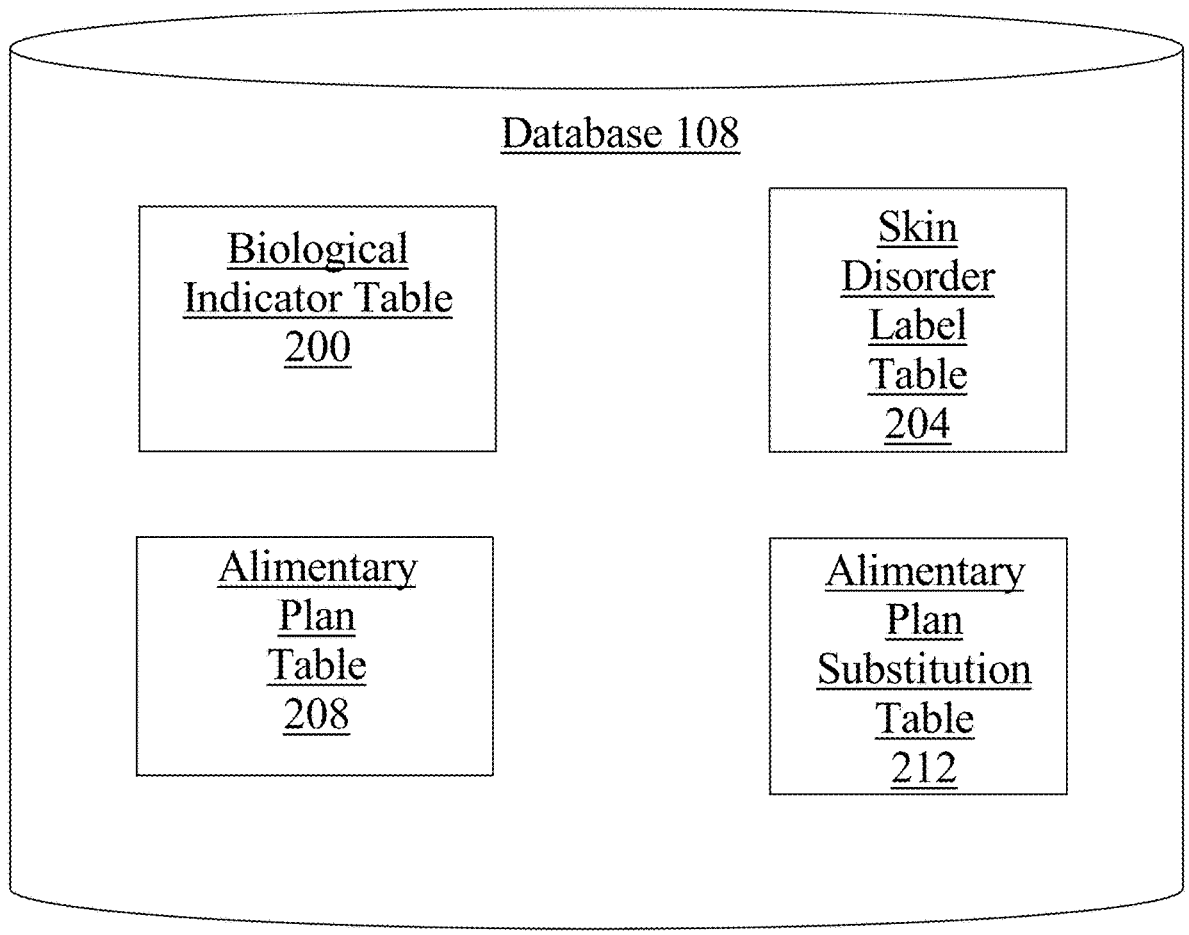
FIG. 2 is a block diagram of an exemplary embodiment of a database.

Referring now to FIG. 2 an exemplary embodiment of a database 108 is illustrated. Database 108 may, as a non-limiting example, organize data stored in the database according to one or more database tables. One or more database tables may be linked to one another by, for instance, common column values. For instance, a common column between two tables of database 108 may include an identifier of alimentary providers, for instance as defined below; as a result, a query may be able to retrieve all rows from any table pertaining to a given alimentary provider. Other columns may include any other category usable for organization or subdivision of data, including types of data, common pathways between, for example, an alimentary combination and a first alimentary provider, or the like; persons skilled in the art, upon reviewing the entirety of this disclosure, will be aware of various ways in which expert data from one or more tables may be linked and/or related to expert data in one or more other tables.

Still referring to FIG. 2, one or more database tables in database 108 may include, as a non-limiting example, a biological indicator table 200. Biological indicator table 200 may be used to store biological indicators and corresponding biological indicator scores, or the like. As another non-limiting example, one or more tables in database 108 may include a skin disorder label table 204. Skin disorder label table 204 may be used to store correlations between biological indicators and potential skin disorders, and the like. Another non-limiting example, one or more tables in database 108 may include an alimentary plan table 208. Alimentary plan table 208 may include, but not limited to alimentary combinations that may treat or prevent a specific skin condition, adverse foods affecting skin disorders, and the like. As another non-limiting example, one or more tables in database 108 may include alimentary plan substitution table 212. Alimentary plan substitution table 212 may include alimentary combinations that may include allowable substitutions for alimentary combinations, substitutions that may create an adverse effect on a skin condition, and the like.

With continued reference to FIG. 1, computing device 104 may be configured to receive an input 112. An "input," as used in this disclosure, may include, but not limited to any medical test, a user's health assessment, a user's nutritional assessment, an assessment conducted in any website related to a skin condition, a direct entry from a user, and the like. Input 112 may include physiological data 116. As used in this disclosure, "physiological data" is any data indicative of a person's physiological state; physiological state may be evaluated with regard to one or more measures of health of a person's body, one or more systems within a person's body such as a circulatory system, a digestive system, a nervous system, or the like, one or more organs within a person's body, and/or any other subdivision of a person's body useful for diagnostic or prognostic purposes. For instance, and without limitation, a particular set of biomarkers, test results, and/or biochemical information may be recognized in each medical field as useful for identifying various disease conditions or prognoses within a relevant field. As a non-limiting example, and without limitation, physiological data 116 describing red blood cells, such as red blood cell count, hemoglobin levels, hematocrit, mean corpuscular volume, mean corpuscular hemoglobin, and/or mean corpuscular hemoglobin concentration may be recognized as useful for identifying various conditions such as dehydration, high testosterone, nutrient deficiencies, kidney dysfunction, chronic inflammation, anemia, and/or blood loss. Input 112 may include physiological data 116 originating from a skin sample, where the skin sample is from a human being. As defined in this disclosure, a skin sample may be a sample that may be removed or photographed from a user's skin to be analyzed for the presence of a skin disorder. The skin sample may be in the form of, for example, an image which may be obtained from photographing the skin directly, photographing a microscope slide containing a skin sample, or the like. The skin sample may be an actual sample obtained from, but not limited to a biopsy. A biopsy may include, but not limited to a punch biopsy, a shave biopsy, and the like. Skin disorders may be the result of an allergic reaction to certain allergens. The use of a patch test may help to determine the allergens causing the disorder. In an embodiment, the physiological data may include a patch test. A skin sample may also be obtained through a skin swab. A skin swab may be used when detecting if the skin is affected by a pathogen such as, but not limited to, a bacterial infection. In another embodiment, the physiological data may include a culture. A culture may be used to determine the type and identity of the pathogen causing the skin disorder.

With continued reference to FIG. 1, physiological state data may include, without limitation, hematological data, such as red blood cell count, which may include a total number of red blood cells in a person's blood and/or in a blood sample, hemoglobin levels, hematocrit representing a percentage of blood in a person and/or sample that is composed of red blood cells, mean corpuscular volume, which may be an estimate of the average red blood cell size, mean corpuscular hemoglobin, which may measure average weight of hemoglobin per red blood cell, mean corpuscular hemoglobin concentration, which may measure an average concentration of hemoglobin in red blood cells, platelet count, mean platelet volume which may measure the average size of platelets, red blood cell distribution width, which measures variation in red blood cell size, absolute neutrophils, which measures the number of neutrophil white blood cells, absolute quantities of lymphocytes such as B-cells, T-cells, Natural Killer Cells, and the like, absolute numbers of monocytes including macrophage precursors, absolute numbers of eosinophils, and/or absolute counts of basophils. Physiological state data may include, without limitation, immune function data such as Interleukine-6 (IL-6), TNF-alpha, systemic inflammatory cytokines, and the like.

Continuing to refer to FIG. 1, physiological state data may include, without limitation, data describing blood-born lipids, including total cholesterol levels, high-density lipoprotein (HDL) cholesterol levels, low-density lipoprotein (LDL) cholesterol levels, very low-density lipoprotein (VLDL) cholesterol levels, levels of triglycerides, and/or any other quantity of any blood-born lipid or lipid-containing substance. Physiological state data may include measures of glucose metabolism such as fasting glucose levels and/or hemoglobin A1-C (HbA1c) levels. Physiological state data may include, without limitation, one or more measures associated with endocrine function, such as without limitation, quantities of dehydroepiandrosterone (DHEAS), DHEA-Sulfate, quantities of cortisol, ratio of DHEAS to cortisol, quantities of testosterone quantities of estrogen, quantities of growth hormone (GH), insulin-like growth factor 1 (IGF-1), quantities of adipokines such as adiponectin, leptin, and/or ghrelin, quantities of somatostatin, progesterone, or the like. Physiological state data may include measures of estimated glomerular filtration rate (eGFR). Physiological state data may include quantities of C-reactive protein, estradiol, ferritin, folate, homocysteine, prostate-specific Ag, thyroid-stimulating hormone, vitamin D, 25 hydroxy, blood urea nitrogen, creatinine, sodium, potassium, chloride, carbon dioxide, uric acid, albumin, globulin, calcium, phosphorus, alkaline phosphatase, alanine amino transferase, aspartate amino transferase, lactate dehydrogenase (LDH), bilirubin, gamma-glutamyl transferase (GGT), iron, and/or total iron binding capacity (TIBC), or the like. Physiological state data may include antinuclear antibody levels. Physiological state data may include aluminum levels. Physiological state data may include arsenic levels. Physiological state data may include levels of fibrinogen, plasma cystatin C, and/or brain natriuretic peptide.

Continuing to refer to FIG. 1, physiological state data may include measures of lung function such as forced expiratory volume, one second (FEV-1) which measures how much air can be exhaled in one second following a deep inhalation, forced vital capacity (FVC), which measures the volume of air that may be contained in the lungs. Physiological state data may include a measurement blood pressure, including without limitation systolic and diastolic blood pressure. Physiological state data may include a measure of waist circumference. Physiological state data may include body mass index (BMI). Physiological state data may include one or more measures of bone mass and/or density such as dual-energy x-ray absorptiometry. Physiological state data may include one or more measures of muscle mass. Physiological state data may include one or more measures of physical capability such as without limitation measures of grip strength, evaluations of standing balance, evaluations of gait speed, pegboard tests, timed up and go tests, and/or chair rising tests.

Still viewing FIG. 1, physiological state data may include one or more measures of cognitive function, including without limitation Rey auditory verbal learning test results, California verbal learning test results, NIH toolbox picture sequence memory test, Digital symbol coding evaluations, and/or Verbal fluency evaluations. Physiological state data may include one or more evaluations of sensory ability, including measures of audition, vision, olfaction, gustation, vestibular function and pain.

Continuing to refer to FIG. 1, physiological state data may include psychological data. Psychological data may include any data generated using psychological, neuro-psychological, and/or cognitive evaluations, as well as diagnostic screening tests, personality tests, personal compatibility tests, or the like; such data may include, without limitation, numerical score data entered by an evaluating professional and/or by a subject performing a self-test such as a computerized questionnaire. Psychological data may include textual, video, or image data describing testing, analysis, and/or conclusions entered by a medical professional such as without limitation a psychologist, psychiatrist, psychotherapist, social worker, a medical doctor, or the like. Psychological data may include data gathered from user interactions with persons, documents, and/or computing devices; for instance, user patterns of purchases, including electronic purchases, communication such as via chatrooms or the like, any textual, image, video, and/or data produced by the subject, any textual image, video and/or other data depicting and/or describing the subject, or the like. Any psychological data and/or data used to generate psychological data may be analyzed using machine-learning and/or language processing modules as described in this disclosure.

Still referring to FIG. 1, physiological state data may include genomic data, including deoxyribonucleic acid (DNA) samples and/or sequences, such as without limitation DNA sequences contained in one or more chromosomes in human cells. Genomic data may include, without limitation, ribonucleic acid (RNA) samples and/or sequences, such as samples and/or sequences of messenger RNA (mRNA) or the like taken from human cells. Genetic data may include telomere lengths. Genomic data may include epigenetic data including data describing one or more states of methylation of genetic material. Physiological state data may include proteomic data, which as used herein is data describing all proteins produced and/or modified by an organism, colony of organisms, or system of organisms, and/or a subset thereof. Physiological state data may include data concerning a microbiome of a person, which as used herein includes any data describing any microorganism and/or combination of microorganisms living on or within a person, including without limitation biomarkers, genomic data, proteomic data, and/or any other metabolic or biochemical data useful for analysis of the effect of such microorganisms on other physiological state data of a person, and/or on prognostic labels and/or ameliorative processes as described in further detail below.

With continuing reference to FIG. 1, physiological state data may include one or more user-entered descriptions of a person's physiological state. One or more user-entered descriptions may include, without limitation, user descriptions of symptoms, which may include without limitation current or past physical, psychological, perceptual, and/or neurological symptoms, user descriptions of current or past physical, emotional, and/or psychological problems and/or concerns, user descriptions of past or current treatments, including therapies, nutritional regimens, exercise regimens, pharmaceuticals or the like, or any other user-entered data that a user may provide to a medical professional when seeking treatment and/or evaluation, and/or in response to medical intake papers, questionnaires, questions from medical professionals, or the like. Physiological state data may include any physiological state data, as described above, describing any multicellular organism living in or on a person including any parasitic and/or symbiotic organisms living in or on the persons; non-limiting examples may include mites, nematodes, flatworms, or the like. Examples of physiological state data described in this disclosure are presented for illustrative purposes only and are not meant to be exhaustive.

With continued reference to FIG. 1, physiological data 116 may include, without limitation any result of any medical test, physiological assessment, cognitive assessment, psychological assessment, or the like. Input 112 may include at least a physiological data 116 from one or more other devices after performance; system 100 may alternatively or additionally perform one or more assessments and/or tests to obtain at least a physiological data 116, and/or one or more portions thereof, on system 100. For instance, at least physiological data 116 may include or more entries by a user in a form or similar graphical user interface object; one or more entries may include, without limitation, user responses to questions on a psychological, behavioral, personality, or cognitive test. For instance, at least a computing device 104 may present to user a set of assessment questions designed or intended to evaluate a current state of mind of the user, a current psychological state of the user, a personality trait of the user, or the like; at least a computing device 104 may provide user-entered responses to such questions directly as at least a physiological data 116 and/or may perform one or more calculations or other algorithms to derive a score or other result of an assessment as specified by one or more testing protocols, such as automated calculation of a Stanford-Binet and/or Wechsler scale for IQ testing, a personality test scoring such as a Myers-Briggs test protocol, or other assessments that may occur to persons skilled in the art upon reviewing the entirety of this disclosure.

With continued reference to FIG. 1, assessment and/or self-assessment data, and/or automated or other assessment results, obtained from a third-party device; third-party device may include, without limitation, a server or other device (not shown) that performs automated cognitive, psychological, behavioral, personality, or other assessments. Third-party device may include a device operated by an informed advisor. An informed advisor may include any medical professional who may assist and/or participate in the medical treatment of a user. An informed advisor may include a medical doctor, nurse, physician assistant, pharmacist, yoga instructor, nutritionist, spiritual healer, meditation teacher, fitness coach, health coach, life coach, and the like.

With continued reference to FIG. 1, physiological data 116 may include data describing one or more test results, including results of mobility tests, stress tests, dexterity tests, endocrine tests, genetic tests, and/or electromyographic tests, biopsies, radiological tests, genetic tests, and/or sensory tests. Persons skilled in the art, upon reviewing the entirety of this disclosure, will be aware of various additional examples of at least a physiological sample consistent with this disclosure.

With continued reference to FIG. 1, physiological data 116 may include one or more user body measurements. A "user body measurement" as used in this disclosure, includes a measurable indicator of the severity, absence, and/or presence of a disease state. A "disease state" as used in this disclosure, includes any harmful deviation from the normal structural and/or function state of a human being. A disease state may include any medical condition and may be associated with specific symptoms and signs. A disease state may be classified into different types including infectious diseases, deficiency diseases, hereditary diseases, and/or physiological diseases. For instance and without limitation, internal dysfunction of the immune system may produce a variety of different diseases including immunodeficiency, hypersensitivity, allergies, and/or autoimmune disorders.

With continued reference to FIG. 1, user body measurements may be related to particular dimensions of the human body. A "dimension of the human body" as used in this disclosure, includes one or more functional body systems that are impaired by disease in a human body and/or animal body. Functional body systems may include one or more body systems recognized as attributing to root causes of disease by functional medicine practitioners and experts. A "root cause" as used in this disclosure, includes any chain of causation describing underlying reasons for a particular disease state and/or medical condition instead of focusing solely on symptomatology reversal. Root cause may include chains of causation developed by functional medicine practices that may focus on disease causation and reversal. For instance and without limitation, a medical condition such as diabetes may include a chain of causation that does not include solely impaired sugar metabolism but that also includes impaired hormone systems including insulin resistance, high cortisol, less than optimal thyroid production, and low sex hormones. Diabetes may include further chains of causation that include inflammation, poor diet, delayed food allergies, leaky gut, oxidative stress, damage to cell membranes, and dysbiosis. Dimensions of the human body may include but are not limited to epigenetics, gut-wall, microbiome, nutrients, genetics, and/or metabolism.

With continued reference to FIG. 1, epigenetic, as used herein, includes any user body measurements describing changes to a genome that do not involve corresponding changes in nucleotide sequence. Epigenetic body measurement may include data describing any heritable phenotypic. Phenotype, as used herein, include any observable trait of a user including morphology, physical form, and structure. Phenotype may include a user's biochemical and physiological properties, behavior, and products of behavior. Behavioral phenotypes may include cognitive, personality, and behavior patterns. This may include effects on cellular and physiological phenotypic traits that may occur due to external or environmental factors. For example, DNA methylation and histone modification may alter phenotypic expression of genes without altering underlying DNA sequence. Epigenetic body measurements may include data describing one or more states of methylation of genetic material.

With continued reference to FIG. 1, gut-wall, as used herein, includes the space surrounding the lumen of the gastrointestinal tract that is composed of four layers including the mucosa, submucosa, muscular layer, and serosa. The mucosa contains the gut epithelium that is composed of goblet cells that function to secrete mucus, which aids in lubricating the passage of food throughout the digestive tract. The goblet cells also aid in protecting the intestinal wall from destruction by digestive enzymes. The mucosa includes villi or folds of the mucosa located in the small intestine that increase the surface area of the intestine. The villi contain a lacteal, that is a vessel connected to the lymph system that aids in removal of lipids and tissue fluids. Villi may contain microvilli that increase the surface area over which absorption can take place. The large intestine lack villi and instead a flat surface containing goblet cells are present.

With continued reference to FIG. 1, gut-wall includes the submucosa, which contains nerves, blood vessels, and elastic fibers containing collagen. Elastic fibers contained within the submucosa aid in stretching the gastrointestinal tract with increased capacity while also maintaining the shape of the intestine. Gut-wall includes muscular layer which contains smooth muscle that aids in peristalsis and the movement of digested material out of and along the gut. Gut-wall includes the serosa which is composed of connective tissue and coated in mucus to prevent friction damage from the intestine rubbing against other tissue. Mesenteries are also found in the serosa and suspend the intestine in the abdominal cavity to stop it from being disturbed when a person is physically active.

With continued reference to FIG. 1, gut-wall body measurement may include data describing one or more test results including results of gut-wall function, gut-wall integrity, gut-wall strength, gut-wall absorption, gut-wall permeability, intestinal absorption, gut-wall barrier function, gut-wall absorption of bacteria, gut-wall malabsorption, gut-wall gastrointestinal imbalances and the like.

With continued reference to FIG. 1, gut-wall body measurement may include any data describing blood test results of creatinine levels, lactulose levels, zonulin levels, and mannitol levels. Gut-wall body measurement may include blood test results of specific gut-wall body measurements including d-lactate, endotoxin lipopolysaccharide (LPS) Gut-wall body measurement may include data breath tests measuring lactulose, hydrogen, methane, lactose, and the like. Gut-wall body measurement may include blood test results describing blood chemistry levels of albumin, bilirubin, complete blood count, electrolytes, minerals, sodium, potassium, calcium, glucose, blood clotting factors, With continued reference to FIG. 1, gut-wall body measurement may include one or more stool test results describing presence or absence of parasites, firmicutes, Bacteroidetes, absorption, inflammation, food sensitivities. Stool test results may describe presence, absence, and/or measurement of acetate, aerobic bacterial cultures, anerobic bacterial cultures, fecal short chain fatty acids, beta-glucuronidase, cholesterol, chymotrypsin, fecal color, *cryptosporidium* EIA, *Entamoeba histolytica*, fecal lactoferrin, *Giardia lamblia* EIA, long chain fatty acids, meat fibers and vegetable fibers, mucus, occult blood, parasite identification, phospholipids, propionate, putrefactive short chain fatty acids, total fecal fat, triglycerides, yeast culture, n-butyrate, pH and the like.

With continued reference to FIG. 1, gut-wall body measurement may include one or more stool test results describing presence, absence, and/or measurement of microorganisms including bacteria, archaea, fungi, protozoa, algae, viruses, parasites, worms, and the like. Stool test results may contain species such as *Bifidobacterium* species, *campylobacter* species, *Clostridium difficile*, *cryptosporidium* species, *Cyclospora cayetanensis*, *Cryptosporidium* EIA, *Dientamoeba fragilis*, *Entamoeba histolytica*, *Escherichia coli*, *Entamoeba histolytica*, *Giardia*, *H. pylori*, *Candida albicans*, *Lactobacillus* species, worms, macroscopic worms, mycology, protozoa, Shiga toxin *E. coli*, and the like.

With continued reference to FIG. 1, gut-wall body measurement may include one or more microscopic ova exam results, microscopic parasite exam results, protozoan polymerase chain reaction test results and the like. Gut-wall body measurement may include enzyme-linked immunosorbent assay (ELISA) test results describing immunoglobulin G (Ig G) food antibody results, immunoglobulin E (Ig E) food antibody results, Ig E mold results, IgG spice and herb results. Gut-wall body measurement may include measurements of calprotectin, eosinophil protein x (EPX), stool weight, pancreatic elastase, total urine volume, blood creatinine levels, blood lactulose levels, blood mannitol levels.

With continued reference to FIG. 1, gut-wall body measurement may include one or more elements of data describing one or more procedures examining gut including for example colonoscopy, endoscopy, large and small molecule challenge, and subsequent urinary recovery using large molecules such as lactulose, polyethylene glycol-3350, and small molecules such as mannitol, L-rhamnose, polyethyleneglycol-400. Gut-wall body measurement may include data describing one or more images such as x-ray, MRI, CT scan, ultrasound, standard barium follow-through examination, barium enema, barium with contract, MRI fluoroscopy, positron emission tomography 9PET), diffusion-weighted MRI imaging, and the like.

With continued reference to FIG. 1, microbiome, as used herein, includes ecological community of commensal, symbiotic, and pathogenic microorganisms that reside on or within any of a number of human tissues and biofluids. For example, human tissues and biofluids may include the skin, mammary glands, placenta, seminal fluid, uterus, vagina, ovarian follicles, lung, saliva, oral mucosa, conjunctiva, biliary, and gastrointestinal tracts. Microbiome may include for example, bacteria, archaea, protists, fungi, and viruses. Microbiome may include commensal organisms that exist within a human being without causing harm or disease. Microbiome may include organisms that are not harmful but rather harm the human when they produce toxic metabolites such as trimethylamine. Microbiome may include pathogenic organisms that cause host damage through virulence factors such as producing toxic by-products. Microbiome may include populations of microbes such as bacteria and yeasts that may inhabit the skin and mucosal surfaces in various parts of the body. Bacteria may include for example Firmicutes species, Bacteroidetes species, Proteobacteria species, Verrumicrobia species, Actinobacteria species, Fusobacteria species, Cyanobacteria species and the like. Archaea may include methanogens such as Methanobrevibacter smithies' and Methanosphaera stadtmanae. Fungi may include *Candida* species and *Malassezia* species. Viruses may include bacteriophages. Microbiome species may vary in different locations throughout the body. For example, the genitourinary system may contain a high prevalence of *Lactobacillus* species while the gastrointestinal tract may contain a high prevalence of *Bifidobacterium* species while the lung may contain a high prevalence of *Streptococcus* and *Staphylococcus* species.

With continued reference to FIG. 1, microbiome body measurement may include one or more stool test results describing presence, absence, and/or measurement of microorganisms including bacteria, archaea, fungi, protozoa, algae, viruses, parasites, worms, and the like. Stool test results may contain species such as Ackerman's muciniphila, Anaerotruncus colihominis, bacteriology, *Bacteroides* vulgates', *Bacteroides-Prevotella, Barnesiella* species, *Bifidobacterium* longarm, *Bifidobacterium* species, Butyrivbrio crossotus, *Clostridium* species, *Collinsella aerofaciens*, fecal color, fecal consistency, *Coprococcus eutactus, Desulfovibrio piger, Escherichia coli, Faecalibacterium prausnitzii*, Fecal occult blood, Firmicutes to Bacteroidetes ratio, *Fusobacterium* species, *Lactobacillus* species, Methanobrevibacter *smithii*, yeast minimum inhibitory concentration, bacteria minimum inhibitory concentration, yeast mycology, fungi mycology, Odoribacter species, *Oxalobacter formigenes*, parasitology, *Prevotella* species, *Pseudoflavonifractor* species, *Roseburia* species, *Ruminococcus* species, *Veillonella* species and the like.

With continued reference to FIG. 1, microbiome body measurement may include one or more stool tests results that identify all microorganisms living a user's gut including bacteria, viruses, archaea, yeast, fungi, parasites, and bacteriophages. Microbiome body measurement may include DNA and RNA sequences from live microorganisms that may impact a user's health. Microbiome body measurement may include high resolution of both species and strains of all microorganisms. Microbiome body measurement may include data describing current microbe activity. Microbiome body measurement may include expression of levels of active microbial gene functions. Microbiome body measurement may include descriptions of sources of disease-causing microorganisms, such as viruses found in the gastrointestinal tract such as raspberry bushy swarf virus from consuming contaminated raspberries or Pepino mosaic virus from consuming contaminated tomatoes.

With continued reference to FIG. 1, microbiome body measurement may include one or more blood test results that identify metabolites produced by microorganisms. Metabolites may include for example, indole-3-propionic acid, indole-3-lactic acid, indole-3-acetic acid, tryptophan, serotonin, kynurenine, total indoxyl sulfate, tyrosine, xanthine, 3-methylxanthine, uric acid, and the like.

With continued reference to FIG. 1, microbiome body measurement may include one or more breath test results that identify certain strains of microorganisms that may be present in certain areas of a user's body. This may include for example, lactose intolerance breath tests, methane-based breath tests, hydrogen-based breath tests, fructose-based breath tests. *Helicobacter pylori* breath test, fructose intolerance breath test, bacterial overgrowth syndrome breath tests and the like.

With continued reference to FIG. 1, microbiome body measurement may include one or more urinary analysis results for certain microbial strains present in urine. This may include for example, urinalysis that examines urine specific gravity, urine cytology, urine sodium, urine culture, urinary calcium, urinary hematuria, urinary glucose levels, urinary acidity, urinary protein, urinary nitrites, bilirubin, red blood cell urinalysis, and the like.

Still with reference to FIG. 1, computing device 104 may be configured to extract a plurality of biological indicators 120 of a disease state from the physiological data 116. The disease state may include a skin disorder. As used in this disclosure, a "skin disorder" is any anomaly that prevents the skin from performing its normal function. Skin disorders may be topical, for example, eczema. Skin disorders may be generated by pathogens, such as, but not limited to bacteria, viruses, and the like. Non-limiting examples of skin disorders caused by pathogens include Impetigo, folliculitis, and boils. Skin disorders may be a secondary condition associated with another disease state. For example, plaque psoriasis, is an auto-immune disorder which causes skin cells to multiply up to 10 times faster than normal. This makes the skin build up into bumpy red patches covered with white scales. Persons skilled in the art, upon reviewing the entirety of this disclosure, will be aware of additional causes of skin disorders. A "biological indicator," as used in this disclosure, is a biological element found in any body fluid, for example blood, skin sample, or the like, that indicates the presence or absence of a condition or a disease. Biological indicators may include, for example, monitoring biological indicators. A "monitoring biological indicator," as used in this specification, is a biological indicator that may be used to assess the progress of a disease or to monitor the effects of a therapeutic agent, such as, for example, a platelet-rich plasma treatment. In another example, a biological indicator may be a diagnostic biological indicator. A "diagnostic biological indicator," as defined in this disclosure is a biological indicator that is used to detect the presence of a disease or a condition of interest. In an embodiment, the plurality of biological indicators comprises a diagnostic indicator. Another example of a biological indicators is a predictive biological indicator. A "predictive biological indicator," as used in this disclosure, is a biological indicator used to predict what group of patients will respond favorably or unfavorably to a particular treatment. Examples of biological indicators that may be used in diagnosing a skin disorder may include, but are not limited to IL-23A, IL23R, IL12B, ZNF313, TNIP1, TNFAIP3, RUNX3, STAT3, TAGAP, ZCH12C, CARD14, CARM1, DDX58, LCE3A/3C/3D, SCCA-2, maspin, cytokeratin14, cytokeratin17, GST-pi, HSP27, 14-3-3sigma, G3MP, Thymosin B4, talinl, actin gamma, filamin, profilin, cytoskeletal calgranulins A, cytoskeletal calgranulins B, Profilin 1, gasdermin A, PA2G4, CBR1, CBR3, GSTP1, SFN, PRDX2, Galectin-7, S100A9, S100A7, keratin 14/16/17, S100A8, S100A9, Stefin A1, slc25a5, serpinb3b, KLK6, and the like.

With continued reference to FIG. 1, computing device 104 may determine a biological indicator score 124 for each biological indicator of the plurality of biological indicators 120. As used in this disclosure, a "biological indicator score" is a numerical measure of the presence of a particular biological indicator. A skin disorder, for example, may be indicated by the presence or absence of a biological indicator score within a particular range. A biological score within a suitable range for a biological indicator may, for example, indicate the absence of a skin disorder. A biological indicator score outside the suitable range may indicate, for example, the presence of a skin disorder. A value considered outside the suitable range may indicate a value that is higher or lower than a value included within the suitable range. A biological indicator score may be a value published in, for example, a research journal. Alternatively, a biological indicator score may be determined by experimentation. For example, an analysis of a skin disorder may include a control experiment to determine the values of a particular biological indicator score that fall within the suitable range. After the control experiment, a skin sample may be analyzed and a measurement for a particular biological indicator score made and compared to the value of the control sample. A patient may be suffering from a skin disorder if, for example, the value of a particular biological indicator score falls outside the suitable range of values of the biological indicator score for the control experiment. A value for the biological indicator score that is higher or lower than the suitable range may result in a positive result for a skin disorder.

Referencing still FIG. 1, computing device 104 may generate a skin disorder classifier 128. Computing device 104 may generate skin disorder classifier 128 by receiving skin disorder training data 132. "Training data," as used herein, is data containing correlations that a machine-learning process may use to model relationships between two or more categories of data elements. For instance, and without limitation, training data 132 may include a plurality of data entries, each entry representing a set of data elements that were recorded, received, and/or generated together; data elements may be correlated by shared existence in a given data entry, by proximity in a given data entry, or the like. Multiple data entries in training data 132 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 132 according to various correlations; correlations may indicate causative and/or predictive links between categories of data elements, which may be modeled as relationships such as mathematical relationships by machine learning processes as described in further detail below. Training data 132 may be formatted and/or organized by categories of data elements, for instance by associating data elements with one or more descriptors corresponding to categories of data elements. As a non-limiting example, training data 132 may include data entered in standardized forms by persons or processes, such that entry of a given data element in a given field in a form may be mapped to one or more descriptors of categories. Elements in training data 132 may be linked to descriptors of categories by tags, tokens, or other data elements; for instance, and without limitation, training data 132 may be provided in fixed-length formats, formats linking positions of data to categories such as comma-separated value (CSV) formats and/or self-describing formats such as extensible markup language (XML), enabling processes or devices to detect categories of data.

Alternatively or additionally, and with continued reference to FIG. 1, training data 132 may include one or more elements that are not categorized; that is, training data 132 may not be formatted or contain descriptors for some elements of data. Machine learning algorithms and/or other processes may sort training data 132 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine learning algorithms, and/or automated association of data in the data entry with descriptors or into a given format. The ability to categorize data entries automatedly may enable the same training data 132 to be made applicable for two or more distinct machine learning algorithms as described in further detail below. Training data 132 used by computing device 104 may correlate any input data as described in this disclosure to any output data as described in this disclosure. Training data may contain entries, each of which correlates a machine learning process input to a machine learning process output, for instance without limitation, one or more elements of biological extraction data to a taste index. Training data may be obtained from previous iterations of machine-learning processes, user inputs, and/or expert inputs. For example, skin disorder training data 132 correlates biological indicators of skin disorder and biological indicator scores to skin disorder labels. As used in this disclosure, "skin disorder labels" are elements of data that may be used to tag a skin disorder. For example, biological indicator TLR-2 and KLK-5, with an elevated biological score the suitable range may be tagged with "Rosacea". Computing device 104 may train skin disorder classifier 128 using skin disorder training data 132.

Still with reference to FIG. 1, computing device 104 may classify, using skin disorder classifier 128, at least one biological indicator and the biological indicator score to a positive result for a skin disorder. A "positive result" for a skin disorder, as defined by this disclosure, is a test result where at least one biological indicator for a skin disorder may be found. A positive result may indicate that the user may be presently suffering from a skin disorder. Alternatively, a positive result may also indicate that the user may develop the skin condition in the future. For example, a positive test for eczema may indicate that biological indicators Serum thymus and activation-regulated chemokine (TARC) are present. A positive result may be obtained based on achieving a certain criterion established for a particular analysis. For example, a skin sample with a 75% departure from the suitable range of type-2 inflammatory biological indicators such as, but not limited to, IL-13, IL-31, CCL17, CCL18, and CCL26 in the blood and cutaneous tissues may be indicative of a positive result for eczema. A description on machine learning and the use of classifiers follows below.

Figure 3:
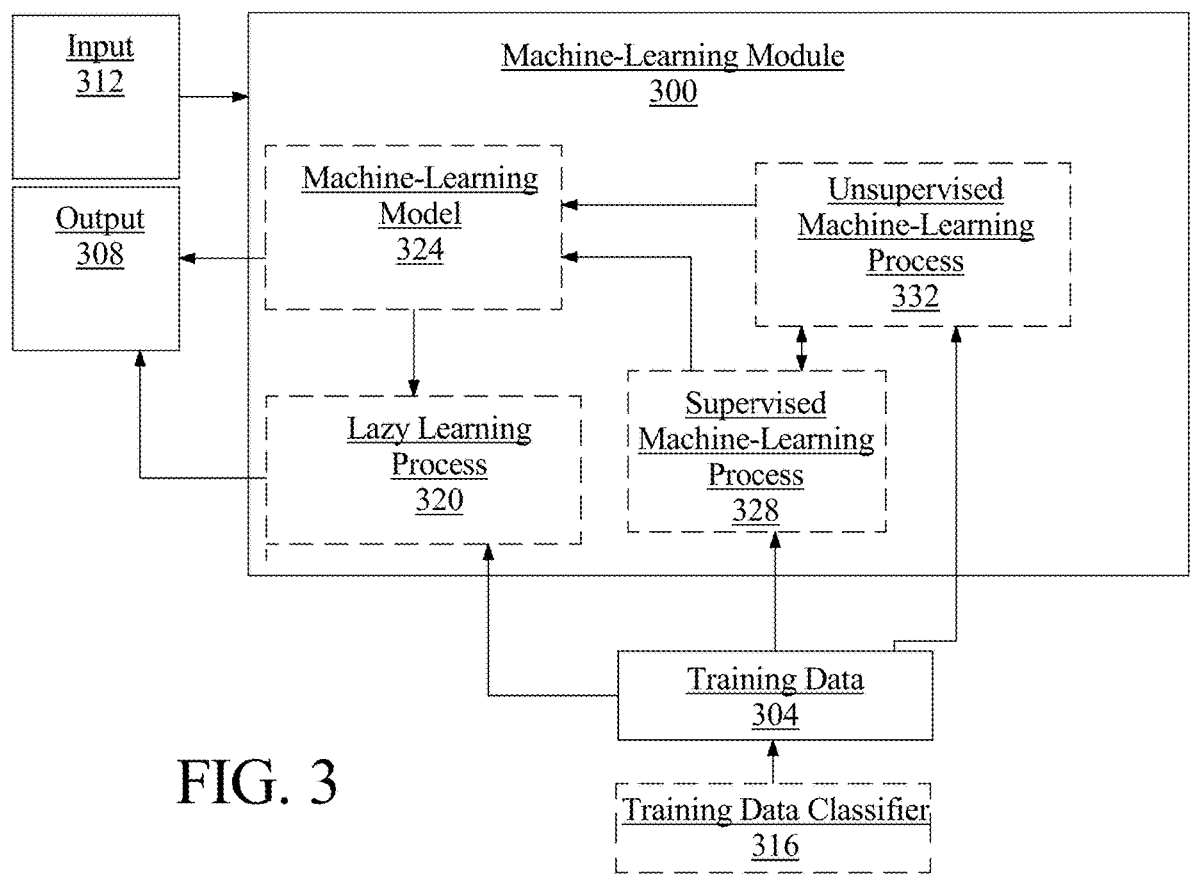
FIG. 3 is a block diagram of an exemplary embodiment of a machine-learning module.

Referring now to FIG. 3, an exemplary embodiment of a machine-learning module 300 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 304 to generate an algorithm that will be performed by a computing device/module to produce outputs 308 given data provided as inputs 312; this is in contrast to a non-machine learning software program where the commands to be executed are determined in advance by a user and written in a programming language.

Still referring to FIG. 3, "training data," as used herein, is data containing correlations that a machine-learning process may use to model relationships between two or more categories of data elements. For instance, and without limitation, training data 304 may include a plurality of data entries, each entry representing a set of data elements that were recorded, received, and/or generated together; data elements may be correlated by shared existence in a given data entry, by proximity in a given data entry, or the like. Multiple data entries in training data 304 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 304 according to various correlations; correlations may indicate causative and/or predictive links between categories of data elements, which may be modeled as relationships such as mathematical relationships by machine-learning processes as described in further detail below. Training data 304 may be formatted and/or organized by categories of data elements, for instance by associating data elements with one or more descriptors corresponding to categories of data elements. As a non-limiting example, training data 304 may include data entered in standardized forms by persons or processes, such that entry of a given data element in a given field in a form may be mapped to one or more descriptors of categories. Elements in training data 304 may be linked to descriptors of categories by tags, tokens, or other data elements; for instance, and without limitation, training data 304 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 3, training data 304 may include one or more elements that are not categorized; that is, training data 304 may not be formatted or contain descriptors for some elements of data. Machine-learning algorithms and/or other processes may sort training data 304 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 304 to be made applicable for two or more distinct machine-learning algorithms as described in further detail below. Training data 304 used by machine-learning module 300 may correlate any input data as described in this disclosure to any output data as described in this disclosure. As a non-limiting illustrative example, skin disorder biological indicators may serve as inputs, outputting other potential health disorders that a may use the same biological indicators.

Further referring to FIG. 3, training data may be filtered, sorted, and/or selected using one or more supervised and/or unsupervised machine-learning processes and/or models as described in further detail below; such models may include without limitation a training data classifier 316. Training data classifier 316 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 300 may generate a classifier using a classification algorithm, defined as a process whereby a computing device and/or any module and/or component operating thereon derives a classifier from training data 304. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 316 may classify elements of training data to classify a skin disorder into categories such as a topical skin disorder, a skin disorder caused by a pathogen activity, a skin disorder that may be related to another condition, and the like.

Still referring to FIG. 3, machine-learning module 300 may be configured to perform a lazy-learning process 320 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 304. Heuristic may include selecting some number of highest-ranking associations and/or training data 304 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 3, machine-learning processes as described in this disclosure may be used to generate machine-learning models 324. A "machine-learning model," as used in this disclosure, is a mathematical and/or algorithmic representation of a relationship between inputs and outputs, as generated using any machine-learning process including without limitation any process as described above and stored in memory; an input is submitted to a machine-learning model 324 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 324 may be generated by creating an artificial neural network, such as a convolutional neural network comprising an input layer of nodes, one or more intermediate layers, and an output layer of nodes. Connections between nodes may be created via the process of "training" the network, in which elements from a training data 304 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 3, machine-learning algorithms may include at least a supervised machine-learning process 328. At least a supervised machine-learning process 328, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include a biological indicator such as interleukin (IL)-23/Th17 as described above as inputs, with at least psoriasis as outputs of a skin disorder, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 304. Persons skilled in the art, upon reviewing the entirety of this disclosure, will be aware of various possible variations of at least a supervised machine-learning process 328 that may be used to determine relation between inputs and outputs. Supervised machine-learning processes may include classification algorithms as defined above.

Further referring to FIG. 3, machine learning processes may include at least an unsupervised machine-learning processes 332. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 3, machine-learning module 300 may be designed and configured to create a machine-learning model 324 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 3, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Referring back to FIG. 1, computing device 104 may generate alimentary plan 136 as a function of the positive result. As defined in this disclosure, an "alimentary plan" is a set of instructions for consumption of a plurality of alimentary compositions that, as used in this disclosure, may help relieve and/or prevent, for example, a skin disorder. "Alimentary compositions," as used in this disclosure, may include any combination of ingredients that may be treated as a meal or a snack or any beverages or combination of beverages that may be consumed by a user. Alimentary plan 136 may include, for example, what type of alimentary compositions a user may want to consume based on the desire to relieve and/or prevent a skin disorder. Alimentary plan 136 may include what specific time of the day the user should consume the alimentary compositions. Alimentary plan 136 may include a list of alimentary compositions to avoid based on a skin disorder. Alimentary plan 136 may include a list of acceptable alimentary compositions substitutes in case an alimentary composition suggested to the user is not available. The alimentary plan may include a list of nutritional supplements that may relieve and/or prevent one or more skin disorders. The alimentary plan may include information as to how to safely take the supplements as well as information regarding any potential adverse effects.

Referring back to FIG. 1, generating alimentary plan 136 may include generating a plurality of alimentary compositions as a function of the positive result. Computing device 104 may order the plurality of alimentary compositions in descending order as a function of a change in the biological indicator score to a suitable range. As used in this disclosure, a "suitable range" is defined as a range of biological indicator scores that would indicate the absence of a skin disorder or that the risk of development of a skin disorder is low. For example, Serum Interleukin-17 (IL-17) may be a biological indicator for acne vulgaris. A user with acne may have Serum IL-17 levels outside the suitable range. An alimentary plan that includes blueberries may relieve and/or prevent acne by inhibiting levels of Serum IL-17 to move the biological indicator score of Serum IL-17 to a suitable range. An alimentary plan that includes 50:50 blueberries-to-honey dew melon may not be as effective in moving the biological indicator score of Serum IL-17 to a suitable range. The plurality of alimentary compositions with the highest change to the suitable range receives the highest order. Computing device 104 may assign the alimentary plan to the plurality of alimentary compositions with the highest order. The alimentary plan assigned by computer device 104 may help relieve and/or prevent a plurality of skin disorders. As an example, a diet rich with blueberries may relive and/or prevent not only acne vulgaris, but, in addition, such a diet may help relieve and/or prevent premature skin aging. In one embodiment, the plurality of alimentary compositions may address a plurality of skin disorders.

Figure 4:
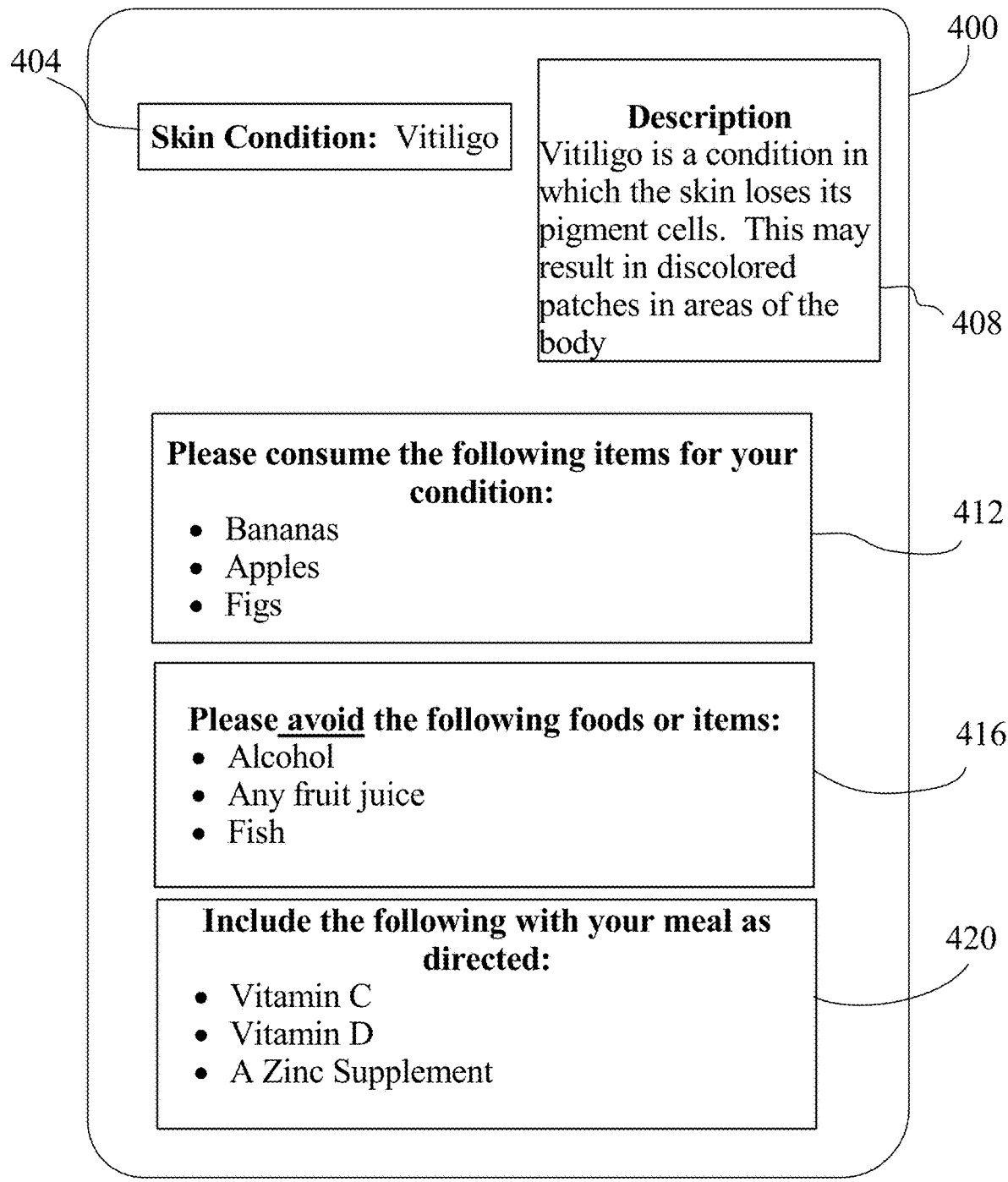
FIG. 4. is a representative illustration of an alimentary plan in a GUI-based device.

Referring now to FIG. 4, an exemplary embodiment of an alimentary plan is described. The alimentary plan may be displayed in a user device 400. For instance, alimentary plan 136 may be displayed in any GUI-based device, such as, but not limited to a mobile telephone, a tablet computer, a desktop computer, and the like. A user may be diagnosed with a skin disorder 404 such as, for example, Vitiligo. Alimentary plan 136 may include description section 408. Description section 408 may describe skin disorder 404. Alimentary plan 136 may include alimentary compositions 412 for the user to consume to relieve and/or prevent Vitiligo. Alimentary plan 136 may include adverse foods 416. Adverse foods 416 may include foods that a user should avoid as the foods listed may aggravate the skin disorder. Nutrients 420 may include a list if supplements that may relieve and/or prevent the skin disorder. Nutrients 420 may include, but not limited to, vitamins, amino acids, minerals, and the like.

Figure 5:
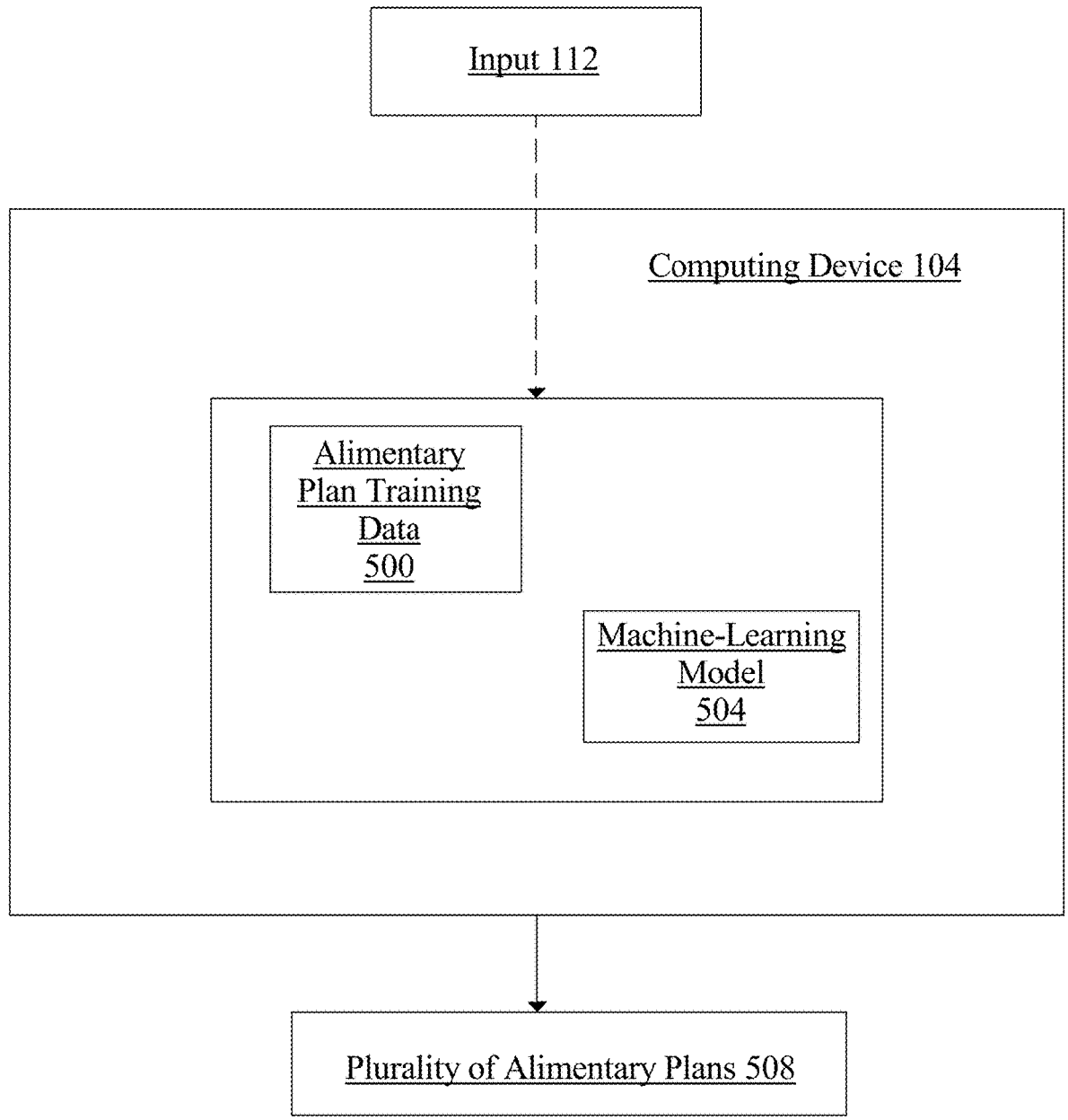
FIG. 5 is a block diagram of an exemplary embodiment of a determination of a plurality of alimentary plans as a function of a machine-learning process.

Now referring to FIG. 5, an exemplary embodiment of the generation of a plurality of alimentary plans 508 implementing a machine learning process is described. Computing device 104 is configured to receive input 112. Computing device 104 may receive alimentary plan training data 500. Alimentary plan training data 500 may be received and/or collected from experts or from users that may have received and used an alimentary plan. The alimentary plan training data 500 may be received as a function of user-entered valuations of alimentary plans, alimentary plan metrics, and/or measurable values. The alimentary plan training set may be received by one or more past iterations of the previous alimentary plan vectors. The alimentary plan training set may be received by one or more remote devices that at least correlate an alimentary plan element and skin disorder metric to a measurable value, wherein a remote device is an external device to computing device 104. A machine-learning model 504 is trained using alimentary plan training data 500. Alimentary plan training data 500 correlates alimentary compositions to effects on skin disorders. Plurality of alimentary plans 508 is outputted as a function of the machine-learning model. The machine-learning model may be implemented, without any limitations, as described earlier in this disclosure. In another embodiment, generating alimentary plan 136 may include outputting a message independent of the presence of the plurality of alimentary plans. For example, Alimentary plan training data 500 may not contain values for a particular skin disorder. As a result, plurality of alimentary plans 508 would not produce suitable plans to treat and/or prevent the skin disorder. As such, a message may be outputted indicating this condition. The message may be outputted directly to a user device, a web page, an email message, and the like. An example of a message may include, "No nutrition suggestions are available for this skin disorder."

Referring back to FIG. 1, computing device 104 may be configured to receive a second input. The second input may include any of the inputs as described for input 112. For example, a second input may correspond to a second skin sample taken after commencing use of alimentary plan 136. A medical professional may want to retest a user to check for changes in the presence or absence of biological indicator 120. A medical professional may want to retest a user to check for changes in biological indicator score 124. Computing device 104 may reclassify at least one biological indicator and the biological indicator score from the second input to a positive result of a skin disorder. Computing device 104 may update the alimentary plan as a function of the second input. As a non-limiting example, biological indicator score 124 of biological indicator 120 may remain unchanged after implementing alimentary plan 136. Alimentary plan 136 generated to treat hidradenitis suppurativa (a boil) which may include, but not limited to lentils and rice, may offer no change in biological indicator score 124 for leukotriene A4-hydrolase (LTA4H). Alimentary plan 136 may be updated to, for example, replace the rice for couscous.

Figure 6:
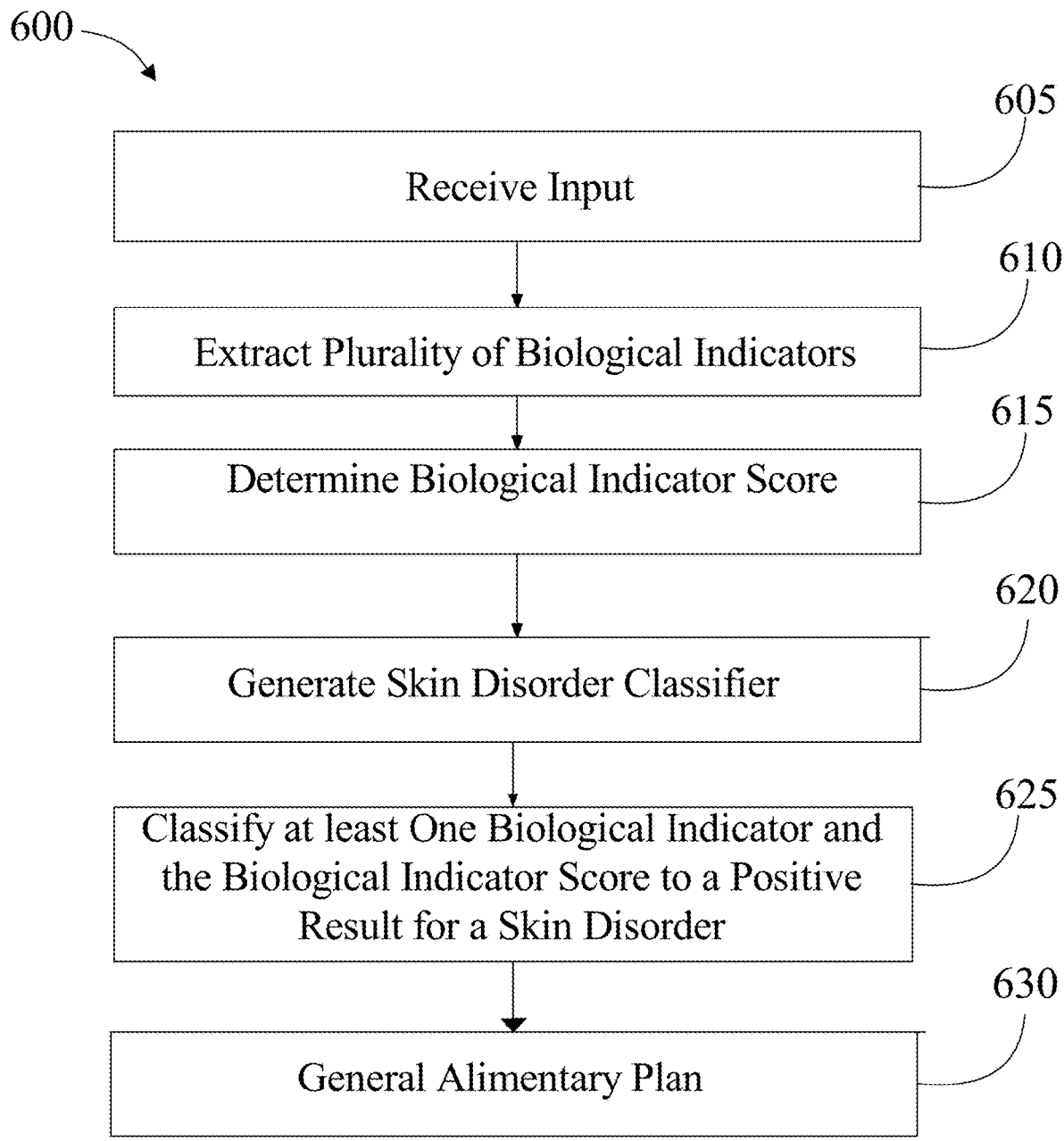
FIG. 6 is a flow diagram illustrating an exemplary embodiment of a method of determining an alimentary plan to manage a skin condition.

Referring now to FIG. 6, an exemplary method 600 for generating an alimentary plan to manage a skin condition is described. At step 605, computing device may receive an input. The input may include physiological data. The input may include physiological data originating from a skin sample. This step may be implemented, without limitation, as described in FIGS. 1-5.

With reference still to FIG. 6, at step 610, computing device may be configured to extract a plurality of biological indicators of a disease state from the physiological data. This step may be implemented, without limitation, as described in FIGS. 1-5.

Still with reference to FIG. 6., at step 615, computing device may determine a biological indicator score for each biological indicator of the plurality of biological indicators. This step may be implemented, without limitation, as described in FIGS. 1-5. A skin disorder, for example, may be indicated by the presence or absence of a biological indicator score within a particular range. A biological score within a suitable range for a biological indicator may, for example, indicate the absence of a skin disorder. A biological indicator score outside the suitable range may indicate, for example, the presence of a skin disorder. A value considered outside the suitable range may indicate a value that is higher or lower than a value included within the suitable range. A biological indicator score may be a value published in, for example, a research journal. Alternatively, a biological indicator may be determined by experimentation. For example, an analysis of a skin disorder may include a control experiment to determine the values of a particular biological indicator that fall within the suitable range. After the control experiment, a skin sample may be analyzed and a measurement for a particular biological indicator made and compared to the value of the control sample.

With continued reference to FIG. 6, at step 620, computing device may generate a skin disorder classifier. The skin order classifier may be generated by the computing device by receiving training data. The computing device may generate a skin disorder classifier by receiving skin disorder training data. Skin disorder training data may correlate biological indicators of skin disorder and biological indicator scores to skin disorder labels. This step may be implemented, without limitation, as described in FIGS. 1-5.

Referring still to FIG. 6, at step 625, computing device may classify, using the skin disorder classifier, at least one biological indicator and the biological indicator score to a positive result for a skin disorder. The use and description of classifiers has been described earlier in this disclosure. This step may be implemented, without limitation, as described in FIGS. 1-5.

With continued reference to FIG. 6, at step 630, computing device may generate an alimentary plan as a function of the positive result. Generating an alimentary plan may include generating a plurality of alimentary compositions as a function of the positive result. A computing device may order the plurality of alimentary compositions in descending order as a function of a change in the biological indicator score to a suitable range. The plurality of alimentary compositions with the highest change to the suitable range receives the highest order. Computing device 104 may assign the alimentary plan to the plurality of alimentary compositions with the highest order. The alimentary plan assigned by computer device 104 may help relieve and/or prevent a plurality of skin disorders. As an example, a diet rich with blueberries may relive and/or prevent not only acne vulgaris, but, in addition, such a diet may help relieve and/or prevent premature skin aging. In one embodiment, the plurality of alimentary compositions may address a plurality of skin disorders. The use and description of classifiers has been described earlier in this disclosure. This step may be implemented, without limitation, as described in FIGS. 1-5.

Additionally or alternatively, with continued reference to FIG. 6, generating an alimentary plan may include outputting a message independent of the presence of the plurality of alimentary plans. For example, Alimentary plan training data 500 may not contain values for a particular skin disorder. As a result, plurality of alimentary plans 508 would not produce suitable plans to treat and/or prevent the particular skin disorder. As such, a message may be outputted indicating this condition. The message may be outputted directly to a user device, a web page, an email message, and the like. An example of a message may include, "No nutrition suggestions are available for this skin disorder." The feature described above may be implemented, without limitation, as described in FIGS. 1-5.

Still referring to FIG. 6, computing device may receive a second input. Computing device may reclassify at least one biological indicator and the biological indicator score from the second input to a positive result of a skin disorder. Computing device may update the alimentary plan as a function of the second input. The feature described above may be implemented, without It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random-access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 7:
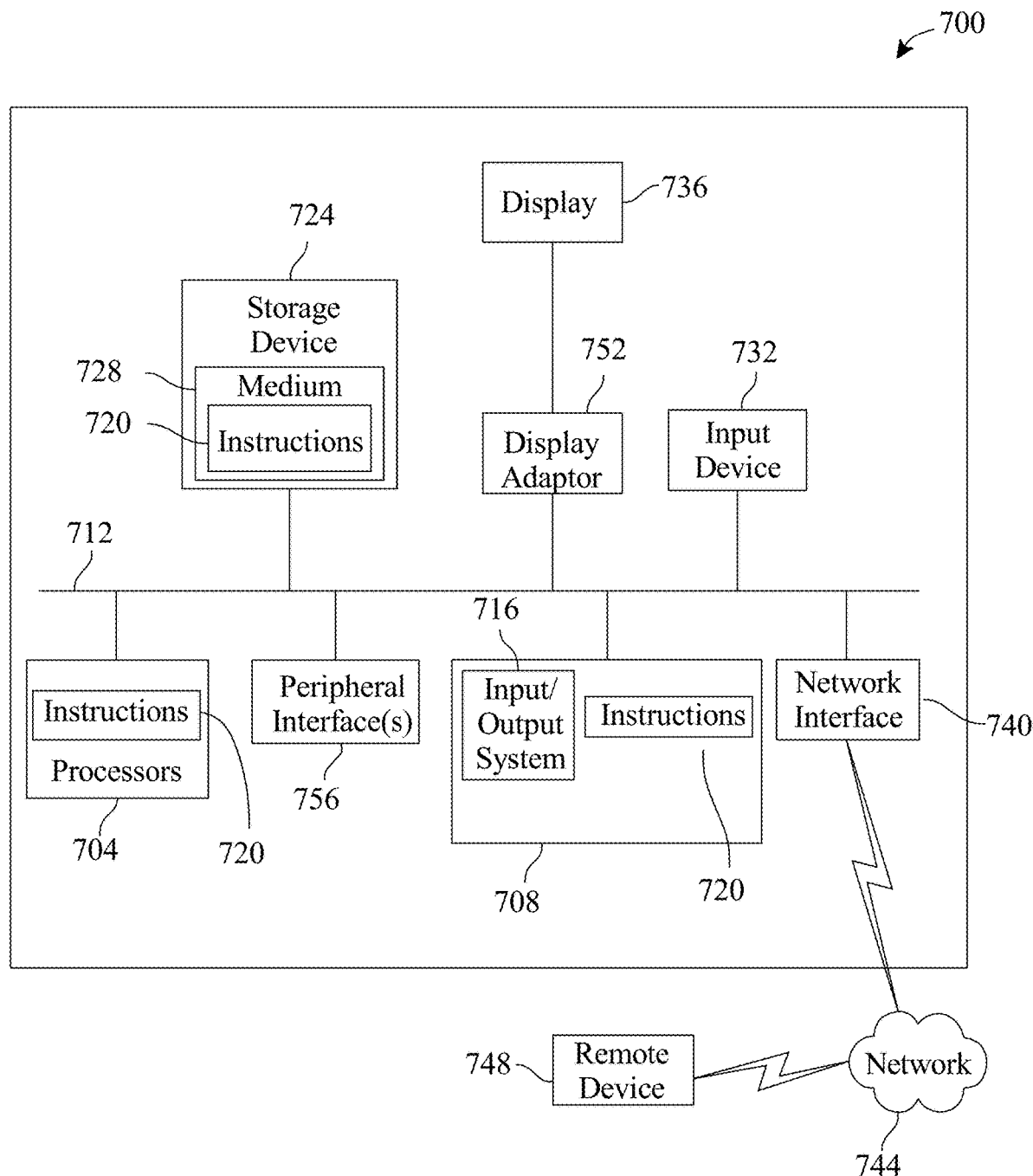
FIG. 7 is a block diagram of a computing system that can be used to implement any one or more of the methodologies disclosed herein and any one or more portions thereof.

FIG. 7 shows a diagrammatic representation of one embodiment of a computing device in the exemplary form of a computer system 700 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 700 includes a processor 704 and a memory 708 that communicate with each other, and with other components, via a bus 712. Bus 712 may include any of several types of bus structures including, but not limited to, a memory bus, a memory controller, a peripheral bus, a local bus, and any combinations thereof, using any of a variety of bus architectures.

Processor 704 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 704 may be organized according to Von Neumann and/or Harvard architecture as a non-limiting example. Processor 704 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating-point unit (FPU), and/or system on a chip (SoC)

Memory 708 may include various components (e.g., machine-readable media) including, but not limited to, a random-access memory component, a read only component, and any combinations thereof. In one example, a basic input/output system 716 (BIOS), including basic routines that help to transfer information between elements within computer system 700, such as during start-up, may be stored in memory 708. Memory 708 may also include (e.g., stored on one or more machine-readable media) instructions (e.g., software) 720 embodying any one or more of the aspects and/or methodologies of the present disclosure. In another example, memory 708 may further include any number of program modules including, but not limited to, an operating system, one or more application programs, other program modules, program data, and any combinations thereof.

Computer system 700 may also include a storage device 724. Examples of a storage device (e.g., storage device 724) include, but are not limited to, a hard disk drive, a magnetic disk drive, an optical disc drive in combination with an optical medium, a solid-state memory device, and any combinations thereof. Storage device 724 may be connected to bus 712 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 724 (or one or more components thereof) may be removably interfaced with computer system 700 (e.g., via an external port connector (not shown)). Particularly, storage device 724 and an associated machine-readable medium 728 may provide nonvolatile and/or volatile storage of machine-readable instructions, data structures, program modules, and/or other data for computer system 700. In one example, software 720 may reside, completely or partially, within machine-readable medium 728. In another example, software 720 may reside, completely or partially, within processor 704.

Computer system 700 may also include an input device 732. In one example, a user of computer system 700 may enter commands and/or other information into computer system 700 via input device 732. Examples of an input device 732 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 732 may be interfaced to bus 712 via any of a variety of interfaces (not shown) including, but not limited to, a serial interface, a parallel interface, a game port, a USB interface, a FIREWIRE interface, a direct interface to bus 712, and any combinations thereof. Input device 732 may include a touch screen interface that may be a part of or separate from display 736, discussed further below. Input device 732 may be utilized as a user selection device for selecting one or more graphical representations in a graphical interface as described above.

A user may also input commands and/or other information to computer system 700 via storage device 724 (e.g., a removable disk drive, a flash drive, etc.) and/or network interface device 740. A network interface device, such as network interface device 740, may be utilized for connecting computer system 700 to one or more of a variety of networks, such as network 744, and one or more remote devices 748 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 744, may employ a wired and/or a wireless mode of communication. In general, any network topology may be used. Information (e.g., data, software 720, etc.) may be communicated to and/or from computer system 700 via network interface device 740.

Computer system 700 may further include a video display adapter 752 for communicating a displayable image to a display device, such as display device 736. Examples of a display device include, but are not limited to, a liquid crystal display (LCD), a cathode ray tube (CRT), a plasma display, a light emitting diode (LED) display, and any combinations thereof. Display adapter 752 and display device 736 may be utilized in combination with processor 704 to provide graphical representations of aspects of the present disclosure. In addition to a display device, computer system 700 may include one or more other peripheral output devices including, but not limited to, an audio speaker, a printer, and any combinations thereof. Such peripheral output devices may be connected to bus 712 via a peripheral interface 756. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve system and methods according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for generating an alimentary plan, the system comprising:
   a computing device configured to:
   receive an input from a user client device operated by a user, the input comprising physiological data from a skin sample, wherein physiological data comprises:
   at least measures of glucose metabolism;
   extract a plurality of biological indicators of a disease state from the physiological data, wherein the plurality of biological indicators comprises:
   at least one biological indicator related to a disease state comprising at least one skin disorder;
   determine a biological indicator score for each biological indicator of the plurality of biological indicators, wherein the biological indicator score for each biological indicator of the plurality of biological indicators correlates to one of a presence or absence of a biological indicator of the plurality of biological indicators;
   generate a skin disorder classifier, wherein generating the skin disorder classifier comprises:
   receiving skin disorder training data correlating biological indicators of skin disorders and biological indicator scores to skin disorder labels, wherein the skin disorder labels correspond to a disease state; and
   training a skin disorder classifier using the skin disorder training data;
   classify, using the skin disorder classifier, the at least one biological indicator and the biological indicator score to a positive result for a skin disorder; and
   generate an alimentary plan, wherein generating the alimentary plan further comprises:
   receiving alimentary plan training data;
   training a machine-learning model using the alimentary plan training data, wherein the alimentary plan training data correlates alimentary compositions to effects on skin disorders;
   outputting a plurality of alimentary plans as a function of the machine-learning model; and
   generating the alimentary plan as a function of the plurality of alimentary plans and the positive result wherein the alimentary plan comprises:
   a plurality of alimentary compositions for consumption to prevent skin disorders;
   a list of alimentary compositions substitutes when the plurality of alimentary compositions for consumption is not available;
   a list of nutritional supplements for consumption to prevent skin disorders;
   a plurality of information on how to safely take the nutritional supplements;
   a plurality of information on adverse effects of the nutritional supplements; and
   set times for consumption of the alimentary compositions.

2. The system of claim 1, wherein generating the alimentary plan further comprises:
   generating a plurality of alimentary compositions as a function of the positive result; and
   ordering the plurality of alimentary compositions in descending order as a function of a change in the biological indicator score to a suitable range, wherein the plurality of alimentary compositions with the highest change to the suitable range receives the highest order.

3. The system of claim 2, wherein the alimentary plan comprises the plurality of alimentary compositions with the highest order.

4. The system of claim 2, wherein the plurality of alimentary compositions addresses a plurality of skin disorders.

5. The system of claim 1, wherein the computing device is further configured to-display, on the user client device operated by a user, the alimentary plan as a function of the positive result.

6. The system of claim 5, wherein generating an alimentary plan further comprises outputting a message independent of the presence of the plurality of alimentary plans.

7. The system of claim 1, wherein the plurality of biological indicators comprises a diagnostic indicator.

8. The system of claim 1, wherein the physiological data comprises results of a patch test.

9. The system of claim 1, wherein the physiological data comprises results of a culture.

10. The system of claim 1, wherein the computing device is further configured to:
receive a second input;
reclassify the at least one biological indicator and the biological indicator score from the second input to a positive result of a skin disorder;
update the alimentary plan as a function of the second input.

11. A method for generating an alimentary plan, the method comprising:
receiving an input from a user client device operated by a user, the input comprising
physiological data from a skin sample wherein physiological data comprises at least measures of glucose metabolism;
extracting a plurality of biological indicators of a disease state from the physiological data, wherein the plurality of biological indicators comprises:
at least one biological indicator related to a disease state comprising at least one skin disorder;
determining a biological indicator score for each biological indicator of the plurality of biological indicators, wherein the biological indicator score for each biological indicator of the plurality of biological indicators correlates to one of a presence or absence of a biological indicator of the plurality of biological indicators;
generating a skin disorder classifier, wherein generating the skin disorder classifier comprises:
receiving skin disorder training data correlating biological indicators of skin disorders and biological indicator scores to skin disorder labels, wherein the skin disorder labels correspond to a disease state; and
training a skin disorder classifier using the skin disorder training data;
classifying, using the skin disorder classifier, the at least one biological indicator and the biological indicator score to a positive result for a skin disorder; and
generating an alimentary plan, wherein generating the alimentary plan further comprises:
receiving alimentary plan training data;
training a machine-learning model using the alimentary plan training data, wherein the alimentary plan training data correlates alimentary compositions to effects on skin disorders;
outputting a plurality of alimentary plans as a function of the machine-learning model; and
generating the alimentary plan as a function of the plurality of alimentary plans and the positive result wherein the alimentary plan comprises:
a plurality of alimentary compositions for consumption to prevent skin disorders;
a list of alimentary compositions substitutes when the plurality of alimentary compositions for consumption is not available;
a list of nutritional supplements for consumption to prevent skin disorders;
a plurality of information on how to safely take the nutritional supplements;
a plurality of information on adverse effects of the nutritional supplements; and
set times for consumption of the alimentary compositions.

12. The method of claim 11, wherein generating the alimentary plan further comprises:
generating a plurality of alimentary compositions as a function of the positive result; and
ordering the plurality of alimentary compositions in descending order as a function of a change in the biological indicator score to a suitable range, wherein the plurality of alimentary compositions with the highest change to the suitable range receives the highest order.

13. The method of claim 12, wherein the alimentary plan comprises the plurality of alimentary compositions with the highest order.

14. The method of claim 12, wherein the plurality of alimentary compositions address a plurality of skin disorders.

15. The method of claim 11, wherein generating an alimentary plan comprises:
displaying on the user client device the alimentary plan as a function of the positive result.

16. The method of claim 15, wherein generating an alimentary plan further comprises outputting a message independent of the presence of the plurality of alimentary plans.

17. The method of claim 11, wherein the plurality of biological indicators comprise a diagnostic indicator.

18. The method of claim 11, wherein the physiological data comprises results of a patch test.

19. The method of claim 11, wherein the physiological data comprises results of a culture.

20. The method of claim 11, further comprising:
receiving a second input;
reclassifying the at least one biological indicator and the biological indicator score from the second input to a positive result of a skin disorder;
updating the alimentary plan as a function of the second input.

* * * * *